(12) United States Patent
Ray et al.

(10) Patent No.: US 7,148,355 B2
(45) Date of Patent: Dec. 12, 2006

(54) PROCESS FOR THE PREPARATION OF REPAGLINIDE

(75) Inventors: Purna Chandra Ray, Delhi (IN); Jayachandra Suresh Babu, Haryana (IN); Mohammad Salman, Plainsboro, NJ (US); Naresh Kumar, Chandigarh (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 349 days.

(21) Appl. No.: 10/490,275

(22) PCT Filed: Sep. 24, 2002

(86) PCT No.: PCT/IB02/03943

§ 371 (c)(1),
(2), (4) Date: Jun. 18, 2004

(87) PCT Pub. No.: WO03/027072

PCT Pub. Date: Apr. 3, 2003

(65) Prior Publication Data

US 2005/0107614 A1    May 19, 2005

(30) Foreign Application Priority Data

Sep. 25, 2001    (IN)    ......................... 983/01

(51) Int. Cl.
*C07D 211/32*    (2006.01)
(52) U.S. Cl. ...................................... 546/234
(58) Field of Classification Search ................. 546/234
See application file for complete search history.

(56) References Cited

U.S. PATENT DOCUMENTS 5,312,924 A    5/1994    Grell et al.    ................. 546/234

OTHER PUBLICATIONS

Grell et al., "Repaglinide and Related Hypoglycemic Benzoic Acid Derivatives", *Journal of Medicinal Chemistry*, 41:5219-5246 (1998) XP000872800, ISSN # 0022-2623.
Guay, "Repaglinide, a Novel, Short-Acting Hypoglycemic Agent for Type 2 Diabetes Mellitus", *Pharmacotherapy*, 18(6):1195-1204 (1998) XP000874581, ISSN # 0277-0008.
*Patent Abstracts of Japan*, vol. 008, No. 168 (C-236) (1984) & Pat. JP 59-065094A—Abstract.

*Primary Examiner*—Patricia L. Morris
(74) *Attorney, Agent, or Firm*—Jayadeep R. Deshmukh, Esq.

(57) ABSTRACT

The present invention relates to a cost effective and industrially advantageous process for the preparation of repaglinide.

10 Claims, No Drawings

PROCESS FOR THE PREPARATION OF REPAGLINIDE

FIELD OF THE INVENTION

The present invention relates to a cost effective and industrially advantageous process for the preparation of repaglinide.

BACKGROUND OF THE INVENTION

Chemically, repaglinide is S(+)-2-ethoxy-4-[N-{1-(2-piperidinophenyl)-3-methyl-1-butyl}aminocarbonylmethyl] benzoic acid having the Formula I,

FORMULA I

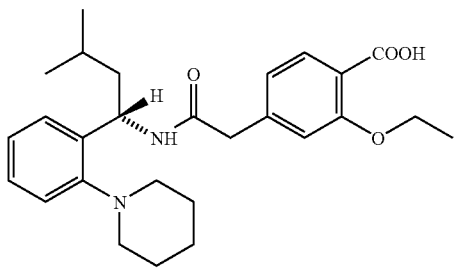

and is known from U.S. Pat. No. 5,312,924. It belongs to a new class of hypoglycemic benzoic acid derivatives. It offers significantly better biological profile as compared to sulphonylurea class of compounds for the treatment of non-insulin dependent diabetes mellitus (NIDDM).

U.S. Pat. No. 5,312,924 describes a process for the preparation of repaglinide which involves the reaction of (S)-amine of Formula II,

FORMULA II

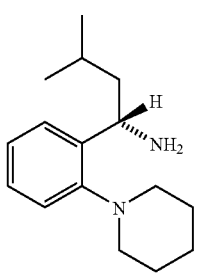

with a carboxylic acid of Formula III,

FORMULA III

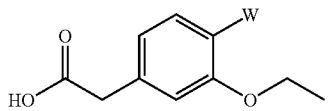

wherein W represents a (protected) carboxy group or a reactive derivative thereof, and cleaving the protecting group, if necessary, to obtain repaglinide of Formula I.

The reaction of the (S)-amine of Formula II with a carboxylic acid of Formula III is carried out in the presence of N,N'-carbonyldiimidazole, N,N'-dicyclohexylcarbodiimide or triphenylphosphine/carbon tetrachloride and triethylanmine. N,N'-carbonyldiimidazole is expensive and gives low yields (50 to 55%) while the use of triphenylphosphine/ carbon tetrachloride necessitates chromatographic purification to obtain repaglinide of desired purity. The use of N,N'-dicyclohexylcarbodiimide generates dicyclohexyl urea as a by-product which can only be removed by repeated crystallizations of the product resulting in increased cycle time and the cost of production. Furthermore, the N,N'-dicyclohexylcarbodiimide is toxic and its use on a commercial scale is undersirable.

Several variations of this method are known which involve the condensation of differently substituted amines and carboxylic acids, followed by suitable chemical modification of the substituents to obtain repaglinide. All of these variations involve additional number of synthetic steps and are therefore not suitable for commercial scale production of repaglinide.

It is, therefore desirable to solve the problems associated with the prior art and to provide an efficient process for the preparation of repaglinide which process improves the economics by employing less expensive and less hazardous raw materials and is more productive. The process avoids the tedious and cumbersome procedures of chromatography or special recrystallization techniques, is economical and convenient to operate on a commercial scale.

The present invention provides a process for the preparation of repaglinide of Formula I comprising:

a) reacting the (S)-amine of Formula II with a protected carboxylic acid of Formula IV,

FORMULA IV

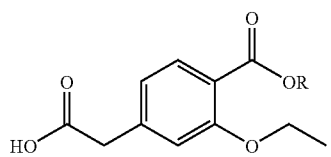

wherein R is a protecting group, in the presence of pivaloyl chloride and a base, and b) removing the protecting group to obtain repaglinide.

The protecting group R in the compound of Formula IV is any carboxylic acid protecting group which is easily removed, such as methyl, ethyl, tert.-butyl, benzyl, p-nitrobenzyl, p-methoxybenzyl, and the like.

The reaction is carried out in the presence of a suitable base which may be either organic or inorganic. Examples of suitable organic bases include amines such as diisopropylamine, dicyclohexylamine, 1,8-diazabicyclo[5.4.0] undec-7-ene, triethylamine, tributylamine, N,N-dimethylaniline, diisopropylethylamine, and the like. Suitable inorganic bases include potassium carbonate, sodium carbonate, and the like.

The reaction may be carried out in a suitable solvent such as dichloromethane, toluene, xylene, and the like. The reaction is carried out at temperatures of between −25° C. and 40° C., but preferably at temperatures of between −10 and 25° C.

The removal of a carboxylic acid protecting group is achieved by suitable methods known in the art such as acidic or basic hydrolysis or hydrogenolysis.

DETAILED DESCRIPTION OF THE INVENTION

In the following section one preferred embodiment has been described by way of example to illustrate the process of the invention. However, it is not intended in any way to limit the scope of the present invention.

EXAMPLE

Preparation of ethyl (S)-2-ethoxy-4-[N-{1-(2-piperidinophenyl)-3-methyl-1-butyl}aminocarbonylmethyl]benzoate Pivaloyl chloride (5.4 g, 45 mmol) was added to a mixture of 3-ethoxy-4-ethoxycarbonyl phenylacetic acid (10.0 g, 40 mmol), toluene (50 ml) and triethylamine (5.0 g, 49 mmol) at −5° C. and stirred for 1 hour. A solution of (S)-3-methyl-1-(2-piperidinophenyl)-1-butylamine (9.8 g, 40 mmol) in toluene (20 ml) was then added at below 10° C. The temperature of the reaction mixture was raised to 30° C. and the mixture stirred overnight. It was then washed with water and saturated sodium bicarbonate solution. Toluene was distilled off under reduced pressure to get the crude product. The crude product was dissolved in toluene (35 ml), hexane (200 ml) was added and the mixture cooled at 0° C. The solid product so obtained was filtered and dried to give 14.0 g of the title compound (Yield: 73%, HPLC Purity 99%).

Preparation of (S)-2-ethoxy-4-[N-{1-(2-piperidinophenyl)-3-methyl-1-butyl}aminocarbonylmethyl]benzoic acid A solution of ethyl (S)-2-ethoxy-4-[N-{1-(2-piperidinophenyl)-3-methyl-1-butyl}-aminocarbonylmethyl]benzoate (20 g, 41.6 mmol) in denatured spirit (200 ml) was stirred at 60–65° C. and 1N sodium hydroxide solution (62 ml) was added. After two hours of stirring at 60° C., the reaction mixture was cooled to 35° C. and pH was adjusted to about 5.0 using 1N hydrochloric acid (about 70 ml). The solution was stirred for 30 minutes at 35–40° C., cooled to 0° C. and stirred at 0 to 5° C. for one hour to get a crystalline product. The crystals were separated by filtration and washed with water. The product was dried at 60–65° C. under vacuum to get repaglinide (17.8 g, Yield: 94%, Assay 99.5% by HPLC).

While the present invention has been described in terms of its specific embodiments, certain modifications and equivalents will be apparent to those skilled in the art and are intended to be included within the scope of the present invention.

The invention claimed is:

1. A process for the preparation of repaglinide of Formula I,

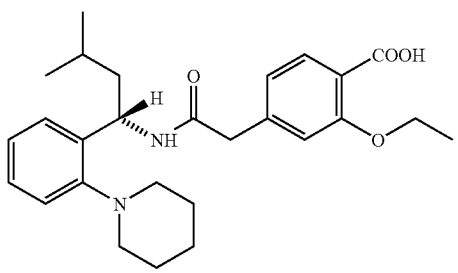

FORMULA I comprising:

a) reacting the (S)-amine of Formula II,

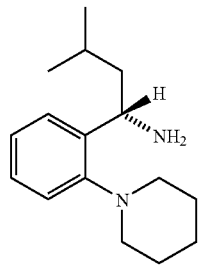

FORMULA II with a protected carboxylic acid of Formula IV,

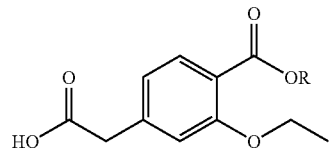

FORMULA IV wherein R is a protecting group, in the presence of pivaloyl chloride and a base, and b) removing the protecting group to obtain repaglinide.

2. The process according to claim 1 wherein the protecting group R is selected from the group consisting of methyl, ethyl, tert.-butyl, benzyl, p-nitrobenzyl, and p-methoxybenzyl.

3. The process according to claim 1 wherein the reaction is carried out in the presence of an organic or inorganic base.

4. The process according to claim 3 wherein the organic base is an amine.

5. The process according to claim 4 wherein the amine is selected from the group consisting of 1,8-diazabicyclo[5.4.0]undec-7-ene, triethylamine, tributylamine, N,N-dimethylaniline, diisopropylethylamine diisopropylamine, and discyclohexylamine.

6. The process according to claim 3 wherein the inorganic base is potassium carbonate or sodium carbonate.

7. The process according to claim 1 wherein the reaction is carried out in a solvent.

8. The process according to claim 7 where the solvent is selected from the group consisting of dichloromethane, toluene and xylene.

9. The process according to claim 1 wherein the reaction is carried out temperatures of between −25° C. and 40° C.

10. The process according to claim 9 wherein the temperature is −10° to 25° C.

* * * * *

UNITED STATES PATENT AND TRADEMARK OFFICE
CERTIFICATE OF CORRECTION

| | | |
|---|---|---|
| PATENT NO. | : 7,148,355 B2 | Page 1 of 1 |
| APPLICATION NO. | : 10/490275 | |
| DATED | : December 12, 2006 | |
| INVENTOR(S) | : Purna Chandra Ray et al. | |

It is certified that error appears in the above-identified patent and that said Letters Patent is hereby corrected as shown below:

Title Page item (30) Foreign Application Priority Data should read:

Sep. 25, 2001   (IN)        983/DEL/2001

Signed and Sealed this

Fourteenth Day of August, 2007

JON W. DUDAS
*Director of the United States Patent and Trademark Office*